(12) United States Patent
Lin et al.

(10) Patent No.: US 6,224,629 B1
(45) Date of Patent: May 1, 2001

(54) BONE SUBSTITUTE COMPOSITION AND PROCESS OF PREPARATION THEREOF

(75) Inventors: Feng-Huei Lin; Chun-Hsu Yao, both of Taipei (TW)

(73) Assignee: Purzer Pharmaceuticals Co. Ltd., Taipei (TW)

( * ) Notice: Subject to any disclaimer, the term of this patent is extended or adjusted under 35 U.S.C. 154(b) by 0 days.

(21) Appl. No.: 09/208,008

(22) Filed: Dec. 9, 1998

(51) Int. Cl.[7] ................................. A61F 2/28; A61F 2/44
(52) U.S. Cl. .................................... 623/16.11; 623/17.11
(58) Field of Search ........................... 623/16, 17, 16.11, 623/17.11, 18.11, 19.11, 20.11; 424/499

(56) References Cited

U.S. PATENT DOCUMENTS

| | | | |
|---|---|---|---|
| 5,352,715 | * 10/1994 | Wallace et al. | 523/115 |
| 5,776,193 | * 7/1998 | Kwan et al. | 623/16 |
| 5,904,718 | * 5/1999 | Jefferies | 623/16 |

FOREIGN PATENT DOCUMENTS

90/13625  * 11/1990  (WO) .

OTHER PUBLICATIONS

Feng–Huel Lin, Chu–Hsu Yao, Jui–Sheng Sun, Haw–Chang Lui, Chin–Wang Huang; "Biological effects and cytotoxicity of the composite composed by tricalcium phosphate and glutaraldehyde cross–linked gelatin"; Biomaterials 19, pp. 905–917, 1998.*

M. P. Ginebra, M. G. Boltong, E. Fernandez, J. A. Planell, F. C. M. Driessens; "Effects of various additives and temperature on some properties of an apatitic calcium phosphate cement"; Journal of Materials Science: Materials in Medicine, pp. 612–616, 1995.*

* cited by examiner

Primary Examiner—Michael J. Milano
Assistant Examiner—Hieu Phan
(74) Attorney, Agent, or Firm—Bacon & Thomas

(57) ABSTRACT

A bone substitute comprises gelatin powder, water, tricalcium phosphate (TCP) powder, and glutaraldehyde. The bone substitute in the present invention, using tricalcium phosphate powder as the major implant ingredient, gelatin powder as glue, and glutaraldehyde as cross-linking agent, can reduce the degradation rate of the bone substitute in the biological body. The present invention also includes the manufacturing procedure of the bone substitute.

8 Claims, 3 Drawing Sheets

BONE SUBSTITUTE COMPOSITION AND PROCESS OF PREPARATION THEREOF

FIELD OF THE INVENTION

The present invention relates to a bone substitute and a process for the preparation thereof.

BACKGROUND OF THE INVENTION

The bone substitutes are mainly used for refilling and recovering materials to repair the cavities of bone defect caused by accidents or bone diseases. Clinically, bone cement is now mostly used for the filling material. The major content of bone cement is polymethymethacrylate (PMMA), which may release its unit, which may interfere with the human-body functions, after implanted into human body. For examples, it may cause uncomfortable feeling due to the decrease of blood pressure, and local temperature increase up to 60° C., due to the polymeric reaction, may cause the death of bone cells. On the other hand, the biocompatibility of PMMA is not very good. It will not form a good linkage with ambient bone tissue after implant, and it will not be absorbed or replaced by the tissue to improve the formation of new bones. Consequently, bone cement is not perfect to be used as a bone substitute.

Besides, bioceramics like hydroxyapatite (HAP) and tricalcium phosphate ($\beta$-TCP) in dense or block are directly filled into bone defect to repair the bone. Though the biocompatibility is good and part of implant materials can be absorbed and replaced by natural bones, the practical implant effect is limited. This is because when the implant powders are filled in, body liquid or blood may often flush the implant materials away from the wound, which may affect the practical implant effect. Even though the implant powders could be made into various porous blocks by molds of various shapes and sizes; however, there could be an important problem occurred during the clinical application. That is: the area and dimension of the bone defect location cannot be exactly same with those we predicted. When this happens, it is necessary to either enlarge the wound or trim the implant block to match each other. This will prolong the operation period and hurt the wound again. Furthermore, there may exit interstice between the wound and implant blocks, which may be obstructive for the cure of wounds.

Consequently, the major direction of development in the implant materials for bone defect is to investigate the composite materials, which are composed of either degradable and synthetic polymers, or mixture of natural polymers and ceramic powders. For example, the composite material composed of Apatite-wollastonite containing glass ceramic-fibrin mixtures was proposed by Yamamuro et al. (1988). Another example is the composite material composed of tricalcium phosphate-gelatin mixtures by Lin et al. (1993). Both materials were studied to become the bone implant substitutes, and both showed good biocompatibility. Furthermore, components for improving bone cell growth, like DMB, BMP and so on, are able to be mixed with these two materials easily during the synthesis process. This is why using above composites as bone implant substitutes became a popular direction of recent studies in this field.

SUMMARY OF THE INVENTION

The objective of the present invention is to provide a bone implant substitute, with good biocompatibility, no toxin, and the capability of improving bone cell growth.

Another objective of the present invention is to provide a manufacturing procedure of bone implant substitute, which provides a cheap and convenient way to produce a good bone implant substitute.

The major components of the bone implant substitute are: (a) gelatin powder, (b) water, (c) tricalcium phosphate (TCP), and (d) glutaraldehyde.

Gelatin (Sigma Chemical Co., U.S.A.), serves as glue, could be extracted and purified from the mammalian skin.

Water is mainly for preparing gelatin solution. Generally speaking, deionized water is preferred. Also, the weight ratio of gelatin powder and deionized water is between 1:20 to 1:5, and 1:10 is preferred.

The TCP powder servers as ceramic powder. In order to reduce the degradation rate, $\beta$-TCP is preferred. $\beta$-TCP, prepared by thermally treating TCP powder at 1000° C., is ground and sieved to become powder form. The weight ratio of TCP powder and gelatin is between 1:1 and 5:1, and 3:1 is preferred.

Glutaraldehyde servers as the cross-linking agent. There are no particular limitations for the amount of added glutaraldehyde. Generally speaking, glutaraldehyde solution (e.g. GA 25% w/w, Sigma Chemical Co., U.S.A.) can be used. The concentrations between 1% and 10% (w/w) are acceptable, and 2% to 8% are preferred.

DETAILED DESCRIPTION OF THE PREFERRED EMBODIMENT

The bone substitute of the present invention can be prepared by the following steps:

(a) solving gelatin powder in the deionized water to obtain a gelatin solution;

(b) adding TCP powder to the gelatin solution, and stirring to obtain a mixture solution; and (c) adding a glutaraldehyde solution to the above mixture solution for cross-linking reaction to the bone substitute.

To reduce the amount of glutaraldehyde in the bone substitute, the bone substitute may be soaked in deionized water furthermore for at least four days.

More detailed examples are used to illustrate the present invention, and these examples are used to explain the present invention. The examples below, which are given simply by way of illustration, must not be taken to limit the scope of the invention.

EXAMPLE 1

10 g of gelatin was solved in 100 ml of deionized water, and 30 g of $\beta$-TCP was added, and all above materials were stirred to form a uniform mixture. Then 1% (w/w) of glutaraldehyde solution was added into the above mixture. This will form cross-linkage with gelatin in the mixture and make the mixture become the bone substitute. A disk-like sample (No. 1), with 6 mm in diameter and 2 mm in thickness, was made by a mold during the polymerization and formation.

EXAMPLES 2 to 4

The disk-like samples (No. 2 to 4) were made by procedures similar to Example 1 except 2% (w/w), 4% (w/w), and 8% (w/w) concentrations of glutaraldehyde were used respectively, instead of 1% (w/w).

Test 1 Determination of Released Glutaraldehyde Concentration

Samples No. 1 to 4 from Examples 1 to 4 were soaked in 20 ml of deionized water for 1, 2, 4, 7, 14, 28, and 42 days to determine the concentration of glutaraldehyde in the soaking solutions. The results are shown on FIG. 1.

Figure 1:
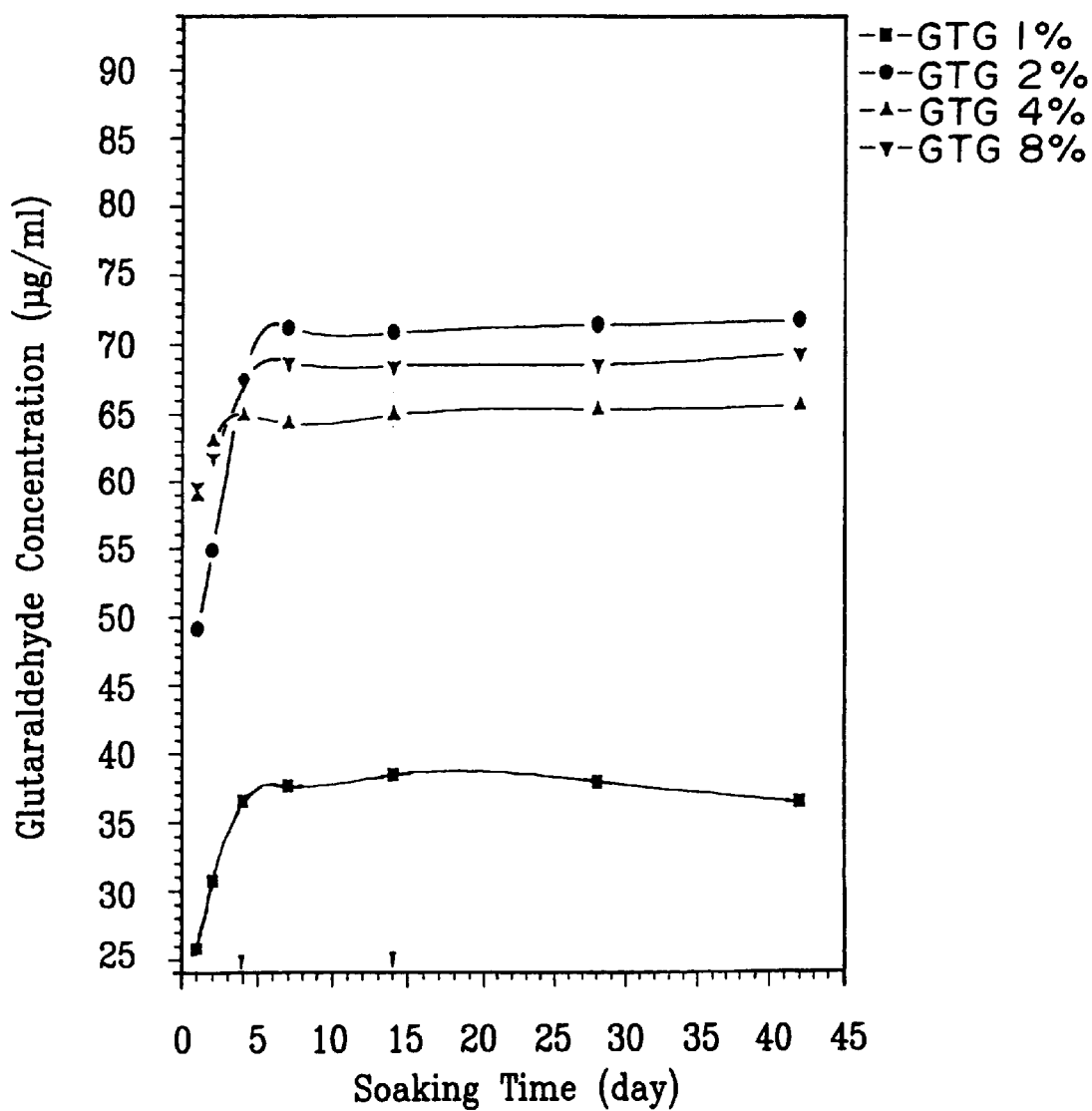
FIG. 1 shows the results of examples 1 to 4; the curves show the released glutaraldehyde concentrations from composites, which were soaked in 20 ml deionized water for 1, 2, 4, 7, 14, 28, and 42 days, respectively.

The results on FIG. 1 show that after 4-day soaking, the concentration of released glutaraldehyde from each sample was close to a stable value. Samples 2 to 4, soaked in solutions added respectively 2% (w/w), 4% (w/w) and 8% (w/w) glutaraldehyde solution as cross-linking agent, released no-difference amount of glutaraldehyde (65–70 $\mu$g/ml).

Test 2 Toxin Determination Of Glutaraldehyde

The cells used in this test are bone cells from the skull of Wistar rats (N.T.U., Taipei, R.O.C.), and 10% of fetal calf serum and 1% of antibiotics were added into the culture medium (Dulmeccos Modified Eagles Minimum Medium, DMEM) used in this test.

To determine the toxin resistance of bone cells to glutaraldehyde solutions, glutaraldehyde solutions were prepared in the concentrations of 10, 20, 30, 40, 50, 60, 70, 80, 90, and 100 ($\mu$g/ml). The bone cell number was counted to see the cell number change after the cell was cultured respectively in the above solutions for two days. In the control group, the phosphate buffer solution (PBS) was used as the culture. After culturing for 2 days, the cell was found at the number of $3.5 \times 10^4$ or around. However, when the bone cells were cultured in different concentrations of glutaraldehyde solutions, the results showed that the cell number was found obviously lower than that in the control group, when the concentration of glutaraldehyde solution increased to 70 $\mu$g/ml. This phenomena indicated that the biotoxin will be resulted in to the bone cell when the concentration of glutaraldehyde solution increased to 70 $\mu$g/ml.

From the results Test 1, the concentration of released glutaraldehyde from each sample was found below 70 $\mu$g/ml. This indicates that all these four GTG composite materials can be directly used in biological body without any soaking processes. Theoretically it will not cause biotoxic reaction.

Test 3 Determination of Released Gelatin Concentration

Samples No. 1 to 4 respectively from Examples 1 to 4 were soaked in 20 ml of deionized water for 1, 2, 4, 7, 14, 28, and 42 days. The gelatin concentrations of the soaking solutions were determined and the results were shown on FIG. 2.

Figure 2:
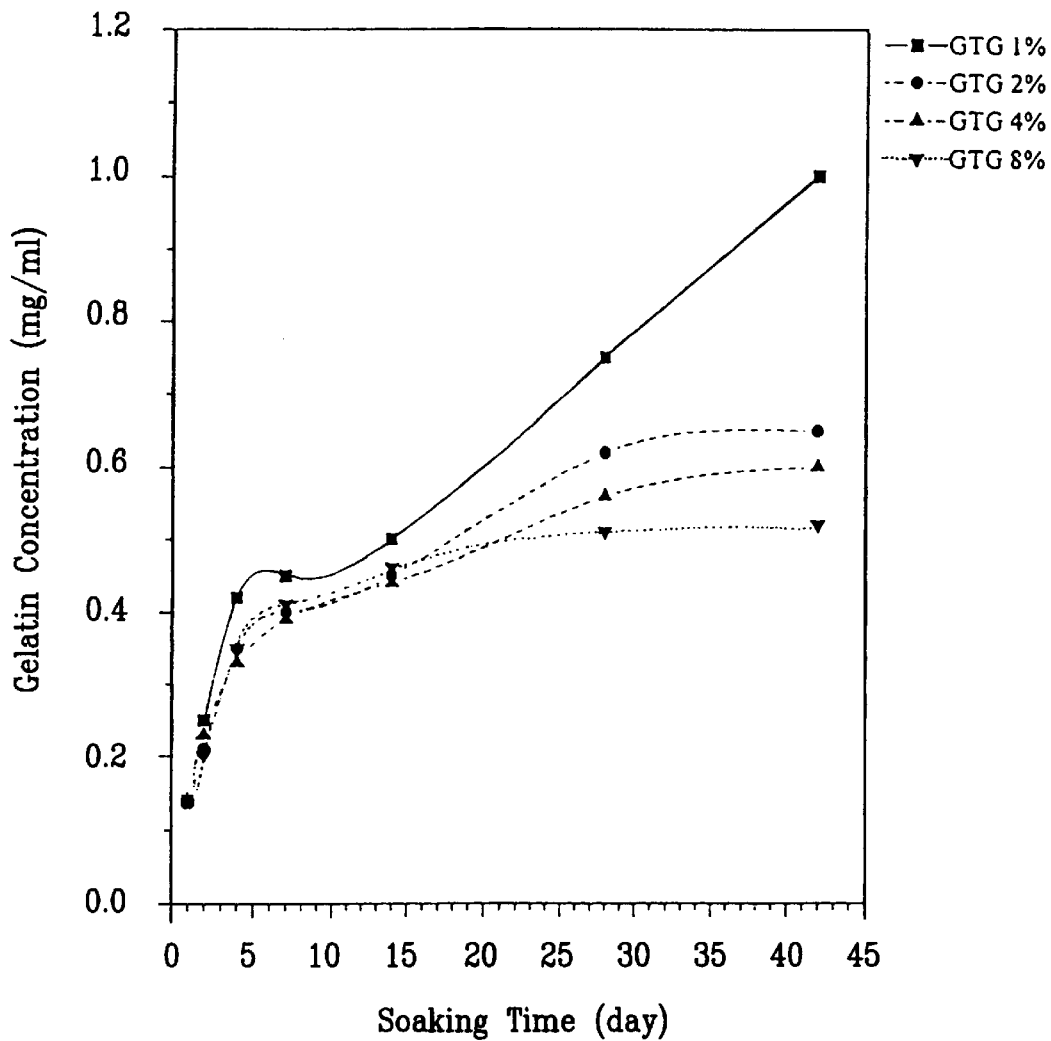
FIG. 2 shows the results of examples 1 to 4; the curves show the released gelatin concentrations from composites, which were soaked in 20 ml deionized water for 1, 2, 4, 7, 14, 28, and 42 days, respectively.

The results on FIG. 2 shows that the gelatin concentration released from each samples obviously increased during the first 7-days soaking, and the data range was around 0.1 to 0.4 mg/ml. This is due to the release of gelatin involved in the cross-linking reaction. During the 7 to 42-days soaking, the gelatin concentration released from each sample was distributed around 0.4 to 0.65 mg/ml. For Samples No. 2 to 4, with 2% (w/w), 4% (w/w), and 8% (w/w) concentrations of glutaraldehyde added as the cross-linking agent, a lower releasing rate was found when a higher concentration of cross-linking agent was added. For Sample No. 1, with 1% (w/w) concentration of glutaraldehyde added as the cross-linking agent, the released gelatin concentration was still found relatively rapid increase. Samples synthesized by different concentrations of the cross-linking agent released different concentrations of gelatin. Increase in the concentration of the cross-linking agent might reduce the releasing rate of gelatin.

Test 4 Determination of the Cell Cultured in Gelatin Solution

Figure 3:
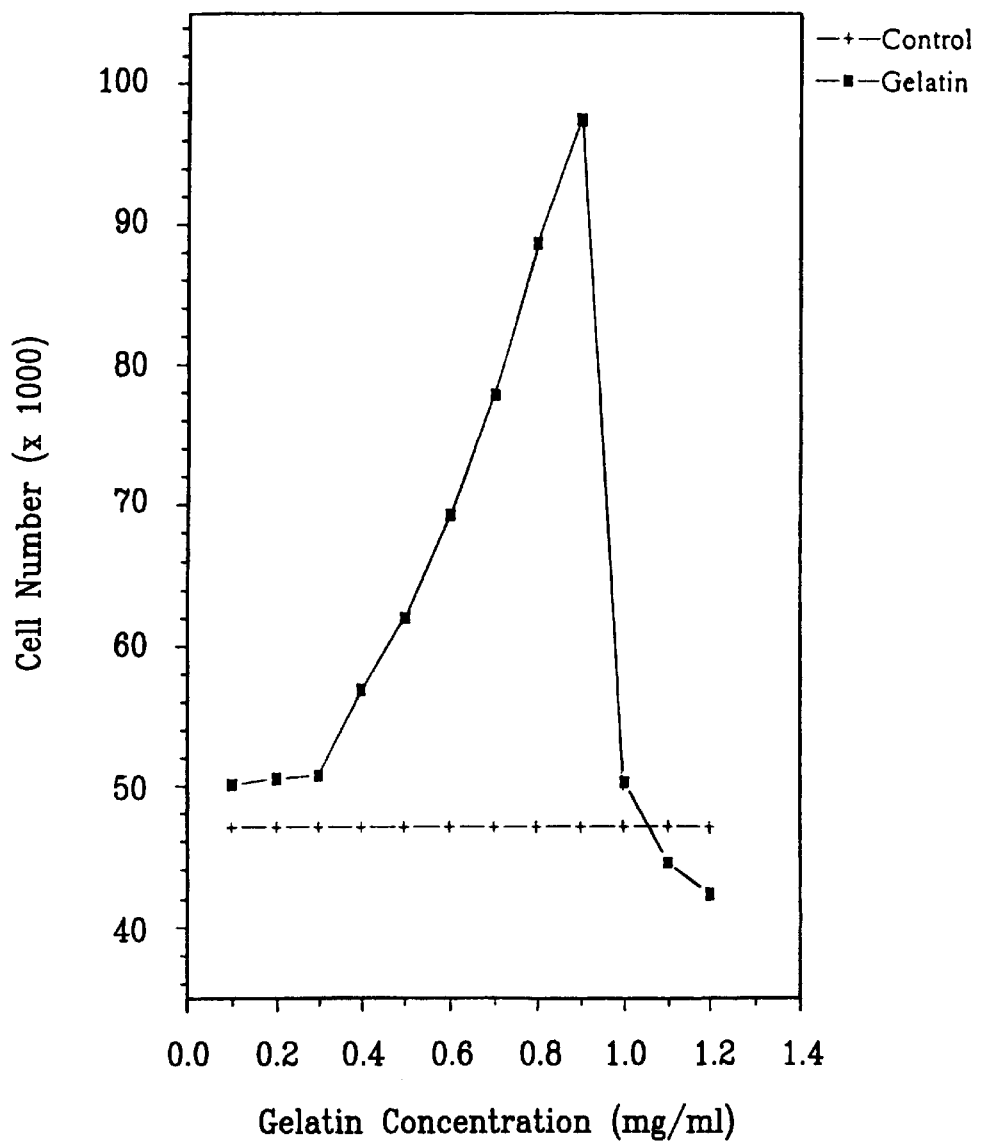
FIG. 3 shows the curves of bone cell number changes after cultured with different concentrations of gelatin solutions.

To evaluate the effect of gelatin to the bone cell and the concentration change to the growth of the bone cell, 0, 100, 200, 300, 400, 500, 600, 700, 800, 900, 1000, 1100, and 1200 $\mu$g/ml of gelatin solutions were used for the bone cell culturing for 2 days. The an optical microscope was used to observe the growth style of bone cells and determine the change of survival bone cells. The results are showed on FIG. 3. In the control group, the bone cells were cultured in PBS, and the cell number was around $4.5 \times 10^4$. For the test groups, the first part is the gelatin concentration of 100 to 300 $\mu$g/ml. In this range the bone cell number did not increase when the concentration of gelatin increased. The cell number was around $5 \times 10^4$. When the gelatin concentration increased to the range of 400 to 900 $\mu$g/ml, the bone cell number increased obviously to $1.0 \times 10$ cell/ml.

From the results of Test 3, during the 7 to 42-days soaking the gelatin concentration released from each sample was distributed around 0.4 to 0.65 mg/ml (the gelatin concentration was in the range that the cell number obviously increased, i.e. 400 to 900 $\mu$g/ml ). In other word, the gelatin released by samples provides a very good gelatin concentration range to help the bone cell growth.

Test 5 Evaluation of Biocompatibility—Body Test

The disk-like sample (No. 5), with 15 mm in diameter and 2 mm in thickness, was made by a mold and procedures similar to Example 1 except 4% concentration of glutaraldehyde was used. After soaked in deionized water for seven days, the samples were put in the 75% alcohol solution for preparation of implant. The evaluation period is up to six months in the experimental design. The bone substitute sample was implanted in the skull of a rabbit, and the skulls were taken out sequentially at the second week, the first month, the second month, the third month and the sixth month after the operation. The skull tissue was then buried and cut into pieces. Optical microscope was used to observe the tissue. In the test groups, four rabbits were used for evaluation except the second-week test, in which only two rabbits were used. In the control group only one rabbit was used at each evaluation stage.

Evaluation Results of Rabbit Skull Implant

Sample No. 5 was macro-observed after it was implanted for one month. In the control group, the defect bone tissue did not get well; there only exited a hard bone membrane. In the test group, Sample No. 5 has firmly combined with ambient tissue, and there were no intervals between Sample No. 5 and the bone tissue.

Then the GTG composite material was implanted for two months and compared with the control group. In the control group, there only exited an layer of fiber tissue; no obvious changes in shape or size could be found. In this case the bone defect cannot get well naturally. In the test group, Sample No. 5 seemed to melt into the ambient bone tissue; the interface between Sample No. 5 and the ambient bone tissue was not as smooth as it looked like before. This phenomena indicated that the new bone tissue gradually formed and the implant material melted.

Three months after the implant, in the control group there were no obvious changes occurred at the bone defect cave; however in the test group the cave was found obviously narrowed.

Six months after the implant, in the control group the natural self-repair at the bone defect cave was limited; however in the test group the bone defect has been repaired, and the implant material has disappeared.

It can be concluded that the bone substitute in the present invention was implanted in the skulls of rabbits, and the evaluation results indicated that by using glutaraldehyde as the cross-linking agent, the composite material, containing tricalcium phosphate and gelatin, could surely delay the material degradation in the biological body. Furthermore, GTG did not cause biotoxic phenomenon, like infection, occurred at the implant location if GTG was soaked in deionized water solvent for more than four days before implant. On the contrary, materials released from the composite increased the self-repair rate of the bone tissue wound. The tissue observation indicated that at the second week of implant, an interface formed between the bone substitute and the bone tissue, and it was not covered with an obvious membrane. At the first month the bone cell broke this interface and attached on the bone substitute. The released materials improved the growth of the new-born bone cells. On the other hand, the new-born bone tissue replaced the place where the bone substitute melted. Two months after the implant, the new bone was more mature in the implanted bone substitute, and the phenomena of bone substitute melting was getting obviously weak, due to the formation of the new bone. At this stage the tendency of either new bone growth or replacing the bone substitute was getting strong. Till the sixth month almost all the bone substitute melted and was absorbed as well as replaced by the new bone cells; the bone defect was almost all repaired to the original natural bone tissue. From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A bone substitute comprising:

(a) gelatin powder (b) water (c) tricalcium phosphate (TCP) powder, and (d) glutaraldehyde wherein the gelatin is extracted and purified from the mammalian skin, and the molecular weight is 60,000–100,000 Dalton.

2. A bone substitute of claim 1 wherein the tricalcium phosphate is $\beta$ phase, and the grain size is about 200–300 $\mu$m.

3. A bone substitute of claim 1 wherein the glutaraldehyde is a glutaraldehyde solution of the concentration between 1% to 10% (w/w).

4. A bone substitute of claim 1 wherein the weight ratio of gelatin and tricalcium phosphate is between 1:5 and 1:1.

5. A bone substitute comprising:

(a) gelatin powder (b) water (c) tricalcium phosphate (TCP) powder, and (d) glutaraldehyde wherein the tricalcium phosphate is $\beta$ phase, and the grain size is about 200–300 $\mu$m.

6. A bone substitute of claim 5, wherein the gelatin is extracted and purified from the mammalian skin, and the molecular weight is 60,000–100,000 Dalton.

7. A bone substitute of claim 5, wherein the glutaraldehyde is a glutaraldehyde solution of the concentration between 1% to 10% (w/w).

8. A bone substitute of claim 5, wherein the weight ratio of gelatin and tricalcium phosphate is between 1:5 and 1:1.

* * * * *